US006417330B1

(12) United States Patent
Mascarenhas et al.

(10) Patent No.: US 6,417,330 B1
(45) Date of Patent: Jul. 9, 2002

(54) INSULIN-LIKE GROWTH FACTOR BINDING PROTEIN VARIANTS

(75) Inventors: Desmond Mascarenhas, Los Altos Hills; David Passmore, Albany; Stephen Danko, San Francisco, all of CA (US)

(73) Assignee: Celtrix Pharmaceuticals, Inc., San Jose, CA (US)

( * ) Notice: Subject to any disclaimer, the term of this patent is extended or adjusted under 35 U.S.C. 154(b) by 0 days.

(21) Appl. No.: 09/322,484

(22) Filed: May 27, 1999

Related U.S. Application Data

(60) Provisional application No. 60/087,559, filed on Jun. 1, 1998.

(51) Int. Cl.$^7$ .................. C07K 17/00; A61K 38/28; A61K 38/00; A61K 38/30
(52) U.S. Cl. .................. 530/350; 530/399; 530/324; 530/303
(58) Field of Search .................. 530/324, 303, 530/350, 399

(56) References Cited

U.S. PATENT DOCUMENTS

| | | |
|---|---|---|
| 4,511,502 A | 4/1985 | Builder et al. |
| 4,511,503 A | 4/1985 | Olson et al. |
| 4,512,922 A | 4/1985 | Jones et al. |
| 5,187,151 A | 2/1993 | Clark et al. |
| 5,288,931 A | 2/1994 | Chang et al. |
| 5,407,913 A | 4/1995 | Sommer et al. |
| 5,410,026 A | 4/1995 | Chang et al. |
| 5,527,776 A | 6/1996 | Carlino et al. |
| 5,629,172 A | 5/1997 | Mascarenhas et al. |
| 5,643,867 A | 7/1997 | Maack et al. |
| 5,663,304 A | 9/1997 | Builder et al. |
| 5,681,818 A | 10/1997 | Spencer et al. |
| 5,683,980 A | 11/1997 | Nilsson et al. |
| 5,723,441 A | 3/1998 | Higley et al. |

FOREIGN PATENT DOCUMENTS

| | | | |
|---|---|---|---|
| WO | WO 89/09268 | * | 10/1989 |
| WO | WO 94 23040 A | | 10/1994 |
| WO | WO 95/03817 | | 2/1995 |
| WO | WO 95 04076 A | | 2/1995 |
| WO | WO 95/13823 | | 5/1995 |
| WO | WO 96/02565 | | 2/1996 |
| WO | WO 96/40722 | | 12/1996 |
| WO | WO 96/40736 | | 12/1996 |

OTHER PUBLICATIONS

Adams et al. (presented Oct. 1995, published 1996). "Pharmacokinetics and Bioavailability of rhIGF–I/IGFBP–3 in Rat and Monkey" *Prog. Growth Factor Res.* 6(2–4):347–356.

Angelloz–Nicoud et al. (1996). "Recombinant Human Insulin–like Growth Factor (IGF) Binding Protein–3 Stimulates Prostate Carcinoma Cell Proliferation via an IGF–dependent Mechanism. Role of Serine Proteases" *Growth Reg.* 6(3):130–136.

Ausubel, F. et al. (1987). *Current Protocols In Molecular Biology*. Green Publishing and Wiley–Interscience: New York, pp. iii–xii.

Baxter et al. (1989). "High Molecular Weight Insulin–like Growth Factor Binding Protein Complex" *J. Biol. Chem.* 264(20):11843–11848.

Baxter et al. (1992). "Structural Determinants for Binary and Ternary Complex Formation between Insulin–like Growth Factor–I (IGF–I) and IGF Binding Protein–3" *J. Biol. Chem.* 267:60–65.

Baxter, C. (1998). "Characterization of the Acid–Labile Subunit of the Growth Hormone–Dependent Insulin–Like Growth Factor Binding Protein Complex" *J. Clin. Endocrinol. Metab.* 67:265–272, 1988.

Bayne et al. (1990). "The Roles of Tyrosines 24, 31, and 60 in the High Affinity Binding of Insulin–like Growth Factor–I to the Type 1 Insulin–like Growth Factor Receptor" *J. Biol. Chem.* 265:15648–15652.

Blum et al. (1991). "Plasma IGFBP–3 Levels as Clinical Indicators" in *Modern Concepts of Insulin–like Growth Factors*. E.M. Spencer, ed. Elsevier: New York. pp. 381–393.

Cascieri et al. (1988). "Structural Analogs of Human Insulin–like Growth Factor (IGF) I with Altered Affinity for Type 2 IGF Receptors" *J. Biol. Chem.* 264:2199–2202.

D'Alessio et al. (1996). "Msh May Play a Conserved Role in Dorsoventral Patterning of the Neuroectoderm" *Mech. Dev.* 58(1–2):217–231.

Jaques et al. (1997). "Nuclear Localization of Insulin–like Growth Factor Binding Protein 3 in a Lung Cancer Cell Line" *Endocrinology* 138(4):1767–1770.

Kruse et al. eds. (1973). *Tissue Culture*. Academic Press: New York, pp. v–xiii.

(List continued on next page.)

*Primary Examiner*—Yvonne Eyler
*Assistant Examiner*—Janet L. Andres
(74) *Attorney, Agent, or Firm*—Foley & Lardner

(57) ABSTRACT

The invention relates to variants of native insulin-like growth factor binding protein 3 (IGFBP-3). Variant IGFBP-3s are disclosed which are modified to be resistant to hydrolysis. Also disclosed are variant IGFBP-3s where the nuclear localization signal (NLS) in native IGFBP-3 is altered. Additionally, amino-terminally extended IGFBP-3s are disclosed which include a variety of N-terminal extensions, including peptide and nucleotide binding domains, specific binding members such as ligand binding domains from receptors or antigen binding domains from immunoglobins, and peptide and protein hormones and growth factors. N-terminally extended IGFBP-3s may comprise hydrolysis-resistant or NLS variant IGFBP-3s.

8 Claims, 1 Drawing Sheet

OTHER PUBLICATIONS

Lavrovsky et al. (1997). "Therapeutic Potential and Mechanism of Action of Oligonucleotides and Ribozymes" *Biochem. Mol. Med.* 62(1):11–22.

Lee et al. (1995). "Purified Rat Acid–Labile Subunit and Recombinant Human Insulin–like Growth Factor (IGF)–Binding Protein–3 Can Form a 150–Kilodalton Binary Complex In Vitro in the Absence of IGFs" *Endocrinology* 136:4982–4989.

LeMotte et al. (1989). "The Homeotic Gene Sex Combs Reduced of Drosophila: Gene structure and embryonic expression" *EMBO J.* 8(1):219–227.

Li et al. (1997). "Nuclear Transport of Insulin–like Growth Factor–I and Insulin–like Growth Factor Binding Protein–3 in Opossum Kidney Cells" *Endocrinology* 138:1763–1766.

Martin et al. (1995). "Complete Sequence of the Bithorax Complex of Drosophila" *Proc. Natl. Acad. Sci. U.S.A.* 92(18):8398–8402.

Nickerson et al. (1997). "Insulin–like Growth Factor Binding Protein–3 Induces Apoptosis in MCF7 Breast Cancer Cells" *Biochem. Biophys. Res. Comm.* 237(3):690–69.

Radulescu. (1994). "Nuclear Localization Signal in Insulin–like Growth Factor–Binding Protein Type 3" *Trends Biochem Sci.* 19(7):278.

Rajah et al. (1997). "Insulin–like Growth Factor (IGF)–binding Protein–3 Induces Apoptosis and Mediates the Effects of Transforming Growth Factor–β1 on Programmed Cell Death Through a p53– and IGF–dependent Mechanism" *J. Biol. Chem.* 272(18):12181–12188.

Riva et al. (1986). "Mammalian Single–Stranded DNA Binding Protein UP I Derived from the hnRNP Core Protein A1" *EMBO J.* 5(9):2267–2273.

Sambrook et al. eds. (1989). *Molecular Cloning: A Laboratory Manual* 2nd ed. vols. 1–3. Cold Spring Harbor Laboratory Press, pp. xi–xxxviii.

Shahrokh et al. (1994). "Major Degradation Products of Basic Fibroblast Growth Factor: Detection of Succinimide and Iso–aspartate in Place of Aspartate" *Pharm. Res.* 11(7):936–944.

Tiranti et al. (1993). "Cloning of Human and Rat cDNAs Encoding the Mitochondrial Single–Stranded DNA–Binding Protein (SSB)" *Gene* 126:219–225.

Zhang et al. (1998). "Expression of Eukaryotic Proteins in Soluble Form in *Escherichia coli*" *Prot. Exp. Purif.* 12:159–165.

Sheldon et al., Proc. Nat. Acad. Sci., vol. 92, pp. 2056–2060, 1995.*

Baxter et al. (1995). "Modulation of human IGF binding protein–3 activity by structural modification," *Prog. Growth Factor Res.* 6(2–4):215–222.

Conover et al. (1995). "Cleavage analysis of insulin–like–growth factor (IGF)–dependent IGF–binding protein–4 proteolysis and expression of protease–resistant IGF–binding protein–4 mutants," *J. Biol. Chem.* 270(9):4395–4400.

Firth et al. (1995). "The role of glycosylation in the action of IGFBP–3," *Prog. in Growth Factor Res.* 6(2–4):223–229.

Firth et al. (1998). "Structural determinants of ligand and cell surface binding of insulin–like growth factor–binding protein–3," *J. Biol. Chem.* 273(5):2631–2638.

Hoeck et al. (1994). "Identification of the major sites of phosphorylation in IGF binding protein–3," *J. Cell. Biochem.* 56(2):262–273.

* cited by examiner

Figure 1

```
1                                                                50
GASSAGLGPV VRCEPCDARA LAQCAPPPAV CAELVREPGC GCCLTCALSE 51                                                               100
GQPCGIYTER CGSGLRCQPS PDEARPLQAL LDGRGLCVNA SAVSRLRAYL 101                                                              150
LPAPPAPGNA SESEEDRSAG SVESPSVSST HRVSDPKFHP LHSKIIIIKK 151                                                              200
GHAKDSQRYK VDYESQSTDT QNFSSESKRE TEYGPCRREM EDTLNHLKFL 201                                                              250
NVLSPRGVHI PNCDKKGFYK KKQCRPSKGR KRGFCWCVDK YGQPLPGYTT 251           264
KGKEDVHCYS MQSK
```

INSULIN-LIKE GROWTH FACTOR BINDING PROTEIN VARIANTS

This application claims priority to under 35 U.S.C. §119(e) U.S. Provisional Application Ser. No. 60/087,559, filed Jun. 1, 1998, the contents of which are incorporated by reference in their entirety.

TECHNICAL FIELD

The invention relates to variants of insulin-like growth factor binding protein (IGFBP) variants, particularly to variants of IGFBP-3 which have resistance to hydrolysis, variants with altered nuclear localization sequences, and to variants with N-terminal extensions.

BACKGROUND ART

Growth factors are polypeptides which stimulate a wide variety of biological responses (e.g. DNA synthesis, cell division, expression of specific genes, etc.) in a defined population of target cells. A variety of growth factors have been identified, including the transforming growth factor beta family (TGF-βs), epidermal growth factor and transforming growth factor alpha (the TGF-αs), the platelet-derived growth factors (PDGFs), the fibroblast growth factor family (FGFs) and the insulin-like growth factor family (IGFs), which includes IGF-I and IGF-II.

IGF-I and IGF-II (the "IGFs")are related in amino acid sequence and structure, with each polypeptide having a molecular weight of approximately 7.5 kilodaltons (kDa). IGF-I mediates the major effects of growth hormone, and is thus the primary mediator of growth after birth. IGF-I has also been implicated in the actions of various other growth factors, since the treatment of cells with such growth factors leads to increased production of IGF-I. In contrast, IGF-II is believed to have a major role in fetal growth. Both IGF-I and IGF-II have insulin-like activities (hence their names), and are mitogenic (stimulate cell division) for the cells in neural tissue.

Almost all IGF circulates in a non-covalently associated complex of IGF-I, insulin-like growth factor binding protein 3 (IGFBP-3) and a larger protein subunit termed the acid labile subunit (ALS), such that very little free IGF-I is detectable. The ternary complex is composed of equimolar amounts of each of the three components. ALS has no direct IGF-binding activity and appears to bind only to the IGF/IGFBP-3 complex (Baxter et al., *J. Biol. Chem.* 264(20): 11843–11848, 1989), although some reports suggest that IGFBP-3 can bind to rat ALS in the absence of IGF (Lee et al., *Endocrinology* 136:4982–4989, 1995). The ternary complex of IGF/IGFBP-3/ALS has a molecular weight of approximately 150 kDa and has a substantially increased half-life in circulation when compared to binary IGF/IGFBP-3 complex or IGF alone (Adams et al., *Prog. Growth Factor Res.* 6(2–4):347–356; presented October 1995, published 1996). This ternary complex is thought to act "as a reservoir and a buffer for IGF-I and IGF-II preventing rapid changes in the concentration of free IGF" (Blum et al. (1991), "Plasma IGFBP-3 Levels as Clinical Indicators" in *Modern Concepts of Insulin-Like Growth Factors*, pp. 381–393, E. M. Spencer, ed., Elsevier, New York). While there is essentially no excess (unbound) IGFBP-3 in circulation, a substantial excess of free ALS does exist (Baxter, *J. Clin. Endocrinol. Metab.* 67:265–272, 1988).

It should be noted that, while IGFBP-3 is the most abundant of the IGF binding proteins ("IGFBPs"), at least five other distinct IGFBPs have been identified in various tissues and body fluids. Although these proteins bind IGFs, they originate from separate genes and have distinct amino acid sequences. Unlike IGFBP-3, other circulating IGFBPs are not saturated with IGFs. IGFBP-3 is the only IGFBP which can form the 150 kDa ternary complex with IGF and ALS. The IGF and ALS binding domains of IGFBP-3 are thought to be in the N-terminal portion of the protein, as N-terminal fragments of the protein isolated from serum retain these binding activities. However, some of the other IGFBPs have also been suggested for use in combination with IGF-I as therapeutics.

The use of IGF/IGFBP-3 complex has been suggested for the treatment of a wide variety of disorders (see, for example, U.S. Pat. Nos. 5,187,151, 5,527,776, 5,407,913, 5,643,867, 5,681,818 and 5,723,441, as well as International Patent Applications Nos. WO 95/03817, WO 95/13823, and WO 96/02565. IGF-I/IGFBP-3 complex is also under development by Celtrix Pharmaceuticals, Inc., as a treatment for several indications, including recovery from burns and recovery from hip fracture surgery.

A prerequisite for the use of IGFBP-3, or any protein, as a component of a therapeutic is that the protein be stable under storage conditions. Many proteins are susceptible to non-enzymatic hydrolysis at sites in the protein which contain a "Asp-Pro" sequence, although not all proteins which contain Asp-Pro are susceptible, nor are all Asp-Pro sites within a protein susceptible to hydrolysis (see for example, Shahrokh et al., 1994, *Pharm. Res.* 11(7): 936–944). It appears that the susceptibility to hydrolysis of any given Asp-Pro sequence is dependent on the local environment of that site in the folded protein. If the Asp-Pro is not present at a site which is accessible to solvent and is not constrained against isomerization, then the site may be susceptible to hydrolysis. It will be apparent that the susceptibility to hydrolysis of Asp-Pro sequences in proteins without known three-dimensional structures cannot be predicted. IGFBP-3 has not been reported to be susceptible to non-enzymatic hydrolysis, and the three-dimensional structure of IGFBP-3 is not known, so susceptibility cannot be predicted.

Several reports have suggested that IGFBP-3 has its own cellular receptor, separate from the IGF receptors, and has its own set of bioactivities (Nickerson et al., 1997, *Biochem. Biophys. Res. Comm.* 237(3):690–69; Rajah et al., 1997, *J. Biol. Chem.* 272(18):12181–12188; Angelloz-Nicoud et al., 1996, *Growth Regul.* 6(3):130–136). Additionally, IGFBP-3, after internalization, has been shown to be targeted to the nucleus, and a nuclear localization signal (NLS) has been identified in the sequence of mature IGFBP-3 (Radulescu, 1994, *Trends Biochem. Sci.* 19(7):278; Jaques et al., 1997 *Endocrinology* 138(4):1767–1770).

Many therapeutic compounds, particularly 'biotech' compounds such as anti-sense oligonucleotides and protein hormones, suffer from problems relating to targeting and half-life. Anti-sense oligonucleotides, for example, generally suffer from both targeting and half-life problems Oligonucleotides which use 'normal' bases and linkages are rapidly eliminated from the circulation by nucleases present in serum. Even if the oligonucleotides are produced using variant nucleosides and/or linkages, they are still rapidly cleared from the circulation, primarily by the kidney and liver. Many protein-based therapeutics (e.g., antibodies, protein hormones and growth factors) suffer from very short circulating half-lives because the proteins are small enough to extravasate, which permits rapid clearance by the kidneys and other organs, or they are specifically cleared by the liver (e.g., antibodies). Covalent modification of proteins (e.g., pegylation) has been attempted to increase circulating half-life, but has been unsatisfactory.

Accordingly, there is a need in the art for stabilized variants of IGFBP-3.

There is also a need in the art for more efficiently delivering therapeutics, such that the therapeutics have increased half-life and bioavailability.

DISCLOSURE OF THE INVENTION

In one embodiment, the invention relates to variants of IGFBP-3 which are stabilized against non-enzymatic hydrolysis. The inventors have found that IGFBP-3 is susceptible to non-enzymatic hydrolysis at a Asp-Pro site in the protein. Additionally, the inventors have surprisingly found that a second site in the protein is susceptible to non-enzymatic hydrolysis. The inventors have designed IGFBP-3 variants which are resistant to non-enzymatic hydrolysis at these sites. Preferred hydrolysis-resistant IGFBP-3 variants include variants of the mature protein in which residues 116 and/or 135 are altered to amino acid residues other than aspartate.

In another embodiment, the invention relates to variants of IGFBP-3 which have altered nuclear localization signals. Preferred variants include mature IGFBP-3 in which residues 228 and/or 230 are altered.

In further embodiments, the invention relates to variants of IGFBP-3 in which an N-terminal extension is added. N-terminally extended IGFBP-3s include as the N-terminal extension, nucleotide-binding sequences, antigen-binding domains; protein hormones and growth factors. The inventors have surprisingly found that large N-terminal extensions may be added to IGFBP-3 without affecting the extended IGFBP-3's ability to bind IGF and form a ternary complex with ALS.

In one N-terminally extended embodiment, the N-terminal extension is a nucleotide binding sequence. The extended IGFBP-3 of this embodiment can be formed into a complex with an IGF (preferably a "null IGF") and a nucleotide that is bound to the N-terminal extension. The complex thus administered results in greatly increased half-life and bioavailability of the nucleotide.

In a further N-terminally extended embodiment, the N-terminal extension is a peptide-binding sequence. The N-terminally extended IGFBP-3 of this embodiment can be formed into a complex with an IGF (preferably a "null IGF") and a peptide. The complex thus administered delivers the peptide, and results in greatly increased half-life and bioavailability of the peptide.

In another N-terminally extended embodiment, the N-terminal extension is an specific binding member. The N-terminally extended IGFBP-3 of this embodiment is formed into a complex with IGF (preferably a "null IGF") and administered to the patient. The complex binds the target of the specific binding member N-terminal extension, and has a greatly increased half-life and bioavailability compared to antibodies, soluble receptors, and other therapeutic specific binding members.

A further N-terminally extended embodiment utilizes a protein growth factor or hormone as the N-terminal extension. The N-terminally extended IGFBP-3 of this embodiment is formed into a complex with IGF (preferably a "null IGF") and administered to the patient. The N-terminal extension moiety can bind to its target receptor and has a greatly increased half-life and bioactivity conferred by being a part of the IGF/IGFBP-3/ALS complex.

BRIEF DESCRIPTION OF THE DRAWINGS

FIG. 1 (SEQ ID NO:1) shows the amino acid sequence (single letter amino acid code) of the naturally occurring $Ala_5$ variant of mature human IGFBP-3.

BEST MODE FOR CARRYING OUT THE INVENTION

Definitions

"Insulin-like growth factor" or "IGF" comprises a family of factors, including, but not limited to, IGF-I and IGF-II. IGF polypeptides have a molecular weight of about 7.5 Kd. IGF includes naturally occurring (native) IGF-I or IGF-II, analogs or variants thereof, and fusions between IGF-I or IGF-II and other amino acid sequences. IGF may be obtained from natural sources or prepared by recombinant means.

As used herein, the term "null IGF-I" refers to IGF molecules which have altered amino acid sequences at one or more sites in the molecule, retain their ability to bind IGFBP-3, but are altered in receptor binding/activation activities (e.g., binding to or activation of the type I or type II IGF receptors or the insulin receptor). Descriptions of null IGF-Is may be found in Cascieri et al. (1988, *Biochemistry* 27:3229–3233; 1989, *J. Biol. Chem.* 264:2199–2202), Bayne et al. (1990, *J. Biol. Chem.* 265:15648–15652) and Baxter et al. (1992, *J. Biol. Chem.* 267:60–65). Examples of null IGF-I include mutants in which one or more of IGF-Is tyrosine residues (i.e., residues 24, 31, or 60, singly or in combination) are replaced with non-aromatic residues (i.e., other than tyrosine, phenylalanine or tryptophan), mutants where amino acid residues 49, 50, 51, 53, 55 and 56, singly or in combination) are altered (for example, where residues 49–50 are altered to Thr-Ser-Ile or where residues 55–56 are altered to Tyr-Gln).

As used herein, "IGFBP-3" refers to insulin-like growth factor binding protein 3. IGFBP-3 is a member of the insulin-like growth factor binding protein family. IGFBP-3 may be from any species, including bovine, ovine, porcine and human, in native-sequence or variant form, including but not limited to naturally-occurring allelic variants (e.g., position 5 of the mature protein is known to be either glycine or alanine), glycosylation variants such as ND variants and hydrolysis resistant variants.

The term "native IGFBP-3" refers to IGFBP-3 having the natural or wild-type sequence for that particular species. The term native IGFBP-3 includes naturally occurring variants (such as the variation at position 5 of the naturally occurring protein).

As used herein, the term "glycosylation variant IGFBP-3" means IGFBP-3s wherein the amino acid residues at the sites of N-linked glycosylation (i.e., positions 89, 109, and 172 of the mature protein) are altered, singly or in combination, to amino acid residues other than asparagine. Examples include e.g.: N89B; N109B; N172B; N89B, N109B; N89B,N172B; N109B,N172B; and N89B,N109B, N172B variants, where B is any amino acid other than asparagine. One preferred group of glycosylation variant IGFBP-3s are the "ND variant IGFBP-3s". ND variant IGFBP-3s are variants of IGFBP-3 in which the amino acids at the sites of N-linked glycosylation (i.e., positions 89, 109, and 172 of the mature protein) are altered to aspartic acid. ND variant IGFBP-3s include e.g.: N89D; N109D; N172D; N89D,N109D; N89D,N172D; N109D,N172D; and N89D, N109D,N172D variants.

The term "hydrolysis-resistant variant IGFBP-3" refers to variants of IGFBP-3 which have been altered from the natural sequence to be more resistant to hydrolysis. Specific examples of hydrolysis-resistant IGFBP-3s include alterations at positions 116 and 135 which alter those positions, singly or in combination, to an amino acid residue other than aspartic acid (e.g., D116J, D135J and D116J,D135J, where J is any amino acid other than aspartic acid). Preferred hydrolysis-resistant variant IGFBP-3 are those variants in which positions 116 and 135 of the mature protein are altered, singly or in combination, to glutamic acid (i.e., D116E, D135E and D116E,D135E).

"NLS variant IGFBP-3" refers to IGFBP-3 variants which have altered nuclear localization signals. The NLS of IGFBP-3 is located in the carboxy-terminal portion of the protein, and includes residues 215 through 232 (Radulescu, 1994, *Trends Biochem Sci.* 19(7):278). Preferred NLS variant IGFBP-3s are those in which residues 228 and 230 of the mature protein are altered to residues other than those in the native sequence (e.g., K228$U_1$, R230$U_2$, where $U_1$ is any amino acid other than lysine and $U_2$ is any amino acid other than arginine), particularly those variants in which position 228 is altered to glutamic acid and/or position 230 is altered to glycine (e.g., K228E, R230$U_2$, K228$U_1$,R230G and K228E,R230G). Additional preferred NLS variants include variants at positions 215,216, and 231.

"N-terminal extended IGFBP-3s" are those IGFBP-3s which have been altered to add additional sequences to the N-terminus of the protein. N-terminal extended IGFBP-3s may be made using any IGFBP-3 sequence, including native IGFBP-3 or variant IGFBP-3 sequences. The N-terminal extension sequences may be of a variety of types, including, but not limited to, nucleotide-binding sequences, peptide-binding sequences, specific binding members, protein hormone sequences, growth factor sequences, enzymes and the like. N-terminal extension sequences may be designed de novo or may be derived from known sequences. For N-terminal extension sequences derived from naturally occurring proteins, cDNAs and genes, the N-terminal extension sequence is preferably derived from the same species as the IGFBP-3 sequence (e.g., for N-terminal extensions of human IGFBP-3, the N-terminal extension is preferably derived from a human protein, cDNA or gene).

"Nucleotide-binding sequences", as used herein, are those amino acid sequences which bind to nucleotide polymers in a sequence-specific or non-sequence specific fashion. Sequence-specific nucleotide-binding sequences include discrete DNA binding domains from transcription factors, such as the homeodomain from the yeast MAT α2 homeodomain protein, homeodomains from *D. melanogaster* homeodomain proteins such as the homeodomain proteins of the bithorax complex (BX-C, Martin et al., 1995, *Proc. Natl. Acad. Sci. U.S.A.* 92(18):8398–8402), sex combs reduced (Scr, LeMotte et al., 1989, *EMBO J.* 8(1):219–227), muscle segment homeobox (msh, D'Alessio et al., 1996, *Mech. Dev.* 58(1–2):217–231), the HOX genes, and others known in the art, zinc finger domains from transcription factors, and the like. Non-sequence specific nucleotide binding sequences include complete or partial proteins, including discrete DNA binding domains, which bind non-specifically to single-stranded DNA or to double-stranded DNA, including mitochondrial single-stranded DNA binding protein (SSB, Tiranti et al., 1993, *Gene* 126:219–225), UP I (Riva et al., 1986, *EMBO J.* 5(9):2267–2273), RecA, and the like.

The term "peptide binding sequence" refers to amino acid sequences which are capable of binding to peptides or proteins in a non-sequence specific manner. The peptide binding sequences may be entire proteins, or may be fragments or domains derived from whole proteins. Examples of proteins which include peptide binding sequences include the proteins known as "chaperones", such as the chaperoning, immunophilins and the heat shock proteins (hsp), as well as the major histocompatibility complex (MHC) proteins. Preferred peptide binding sequences include gp96, hsp70, hsp90, and MHC class I and class II, particularly the extracellular domains. The products of the *E. coli* genes DsbA and DsbC and their homologues are not included within the term "peptide binding sequence" as used herein.

"Specific binding members" are sequences which bind specific target sequences. The target sequences may be proteins, carbohydrates, nucleotides or any other molecules for which a specific binding member is available. Antibodies and fragments or components thereof (i.e., antigen binding sequences) are one group of preferred specific binding members. The antigen binding sequence may be the entire antibody heavy chain, a single chain antibody, an antibody fragment such as Fab and F(ab')$_2$ or a segment of an antibody chain such as the variable region of the heavy chain ($V_H$), Fd segment of the heavy chain (which comprises the $V_H$ domain and the first constant domain), sFv, one or more of the complementarity determining regions (CDRs) of an immunoglobin heavy chain that is specific for the target sequence. Alternately, a ligand binding sequence may be utilized as the specific binding member. Ligand binding sequences may be derived from cellular receptors, and may include soluble forms of the receptor, the extracellular domain or a fragment thereof.

The terms "protein hormone" and "growth factors" refer to peptides and proteins which act in an endocrine, paracrine, or autocrine fashion. Protein hormones and growth factors are well known in the art, and comprise a number of families. Examples of growth factors include, but are not limited to: the transforming growth factors (TGFs), including the TGF-αs, such as TGF-α, epidermal growth factor (EGF) and TGF-αHIII, and the TGF-β superfamily, which includes the TGF-βs, the bone morphogenetic proteins (BMPs), the activins, inhibins and others; the fibroblast growth factor (FGF) family, including FGF1 through at least FGF-18; the vascular endothelial cell growth factor (VEGF) family, including VEGF, VEGF2, VEGFC, and VEGFD; the platelet derived growth factor (PDGF) family, including the AA, AB and BB isoforms of PDGF; the insulin like growth factors (IGFs), including native sequence IGF-I, native sequence IGF-II, des(1–3)IGF-I and other IGF variants known to the art; as well as other growth factors as are known in the art. Protein hormones include growth hormone, neuropeptides such as vasoactive intestinal peptide (VIP), neurokinin A (NKA),calcitonin gene-related peptide (CGRP),pituitary adenylate cyclase activating peptide (PACAP), neuropeptide Y (NPY), and somatostatin.

When N-terminally extended IGFBP-3s comprise an enzyme, the enzyme may be any enzyme that will act on a target cell. IGFBP-3 having native sequence at positions 215, 216, 228, 230 and 231 of the mature protein has been shown to be translocated to the nucleus of dividing cells, but not quiescent cells (Li et al., 1997, *Endocrinology* 138:1763–1766). It should be noted that enzymes that are useful as N-terminal extensions in accordance with the invention do not include glutathione-S-transferase or β-galactosidase. Variant IGFBP-3 comprising an enzyme as the N-terminal extension acts as a platform to deliver the N-terminal extension enzyme to the nuclei of rapidly dividing cells. In one preferred embodiment, the N-terminal extension enzyme is an enzyme that acts on nucleic acids, such as an integrase, a ribonuclease (RNase), restriction endonuclease, or exonuclease. Delivery of enzymes which cut or degrade nucleic acids (e.g. nucleases) can alter the growth kinetics, or even kill, rapidly dividing cells, such as cancer cells. In a further preferred embodiment, the N-terminal extension enzyme is an enzyme which confers drug sensitivity to the target cell, such as the herpes simplex v (HSV) or cytomegalovirus (CMV) thymidine kinase (TK) gene. Cells expressing HSV or CMV TK become sensitive to the drugs acyclovir and ganciclovir, and so the target cells may be killed by administration of acyclovir or ganciclovir concurrent with or following administration of N-terminally extended IGFBP-3 comprising HSV or CMV TK.

A "therapeutic nucleotide" is a poly or oligonucleotide which may be administered to cause a pharmacological effect by altering transcription and/or translation of specific genes and mRNAs. Preferred therapeutic nucleotides are antisense oligonucleotides and ribozymes. An antisense oligonucleotide is normally a single stranded oligonucleotide which is designed to form a duplex with a particular mRNA within the target cell, resulting in arrest of translation and/or degradation of the targeted mRNA. Ribozymes are ribonucleotides which have enzymatic activity and can be designed to cleave specific sequences (see, for example, Lavrovsky et al., 1997, *Biochem. Mol. Med.* 62(1):11–22). Unmodified phosphodiester oligonucleotides may be used, these are less preferred, as they are highly sensitive to nucleases present in serum. Modified oligonucleotides (which have backbone chemistries other than phosphodiester, including phosphorothioate and methylphosphonate) are preferred oligonucleotides for use in the instant invention.

Hydrolysis-resistant variant IGFBP-3 has utility in all applications for which native IGFBP-3 has utility. NLS-variant IGFBP-3 also has utility in all applications for which native IGFBP-3 has utility. These variant IGFBP-3s may be used as a therapeutics for inhibiting the action of IGF, or they may be administered as a complex with IGF for treatment of a wide variety of disorders.

N-terminal extended IGFBP-3s have a variety of utilities, depending on the nature of the N-terminal extension. For example, N-terminal extended IGFBP-3 with a nucleotide binding sequence as the N-terminal extension may be used for delivery of nucleotide based drugs, such as anti-sense oligonucleotides. N-terminal extended IGFBP-3 with a peptide binding sequence or a specific binding member as the N-terminal extension may be used, for example, for delivery of peptide and protein-based therapeutics and as a sustained-release delivery agent for immunization. N-terminal extended IGFBP-3 with a protein hormone or growth factor is useful for sustained delivery of the protein hormone or growth factor which comprises the N-terminal extension.

The variant IGFBP-3s of the invention are preferably produced by recombinant expression methods. In general, a DNA sequence encoding the variant is created by, for example, de novo synthesis or by site-directed mutagenesis of a pre-existing DNA encoding for IGFBP-3. For de novo synthesis, the DNA sequence encoding the variant IGFBP-3 will normally be produced in multiple segments (native IGFBP-3 is 264 amino acids, which requires in a DNA molecule at least 792 nucleotides long), which are ligated together to produce the full DNA sequence. Methods for creating specific alterations in a particular DNA sequence are quite well known, and it will be apparent to one of skill in the art that any method useful for making alterations in DNA sequence may be used for the alteration of DNA sequences to create a DNA sequence encoding a variant IGFBP-3 of the invention.

Variant IGFBP-3s may be produced as a fusion protein or by "direct expression" (production of the variant IGFBP-3 without an associated signal or secretion sequence or fusion partner). Suitable fusion partners for fusion protein production of variant IGFBP-3s include glutathione-S-transferase (GST), secretion signal sequences operable in the recombinant host cell, and the solubility enhancing fusion partners disclosed in U.S. Pat. No. 5,629,172 (e.g., leaderless DsbA). In the case of production as a fusion protein, the fusion protein may be cleaved to remove the fusion partner by action of a protease within the host cell or in vitro after collection of the expressed fusion protein. Such cleavage will normally require the presence of a protease target sequence inserted between the fusion partner and the variant IGFBP-3 sequence. Any target sequence/protease combination that provides sufficient activity and specificity may be utilized, although the ubiquitin/ubiquitin hydrolase and HRV protease 3C systems are preferred.

Normally, the DNA encoding the variant IGFBP-3 is inserted into an expression vector (a DNA construct containing the necessary sequences in proper arrangement to effect transcription and translation of a mRNA for the variant IGFBP-3), which is then introduced into a recombinant host cell. Recombinant expression vectors normally contain sequences necessary for the initiation of transcription and translation, including promoters, operators, enhancers, ribosome binding sites, and the like, as well as transcriptional termination sites and sequences necessary for proper mRNA processing (such as poly-A addition sites for eukaryotic host cells). Preferably, the promoters, operators, and/or enhancers are inducible, such that the expression of the variant IGFBP-3 sequence is regulated by the presence or absence of a particular compound (e.g., use of the lac operon confers regulation by lactose and lactose analogues). Recombinant expression vectors for use in eukaryotic host cells may further contain a heterologous intron with the appropriate signals for processing of the intron, as this has been shown to increase mRNA export in some systems. Preferred expression constructs for use in prokaryotic cells are disclosed in International Patent Application No. WO 96/40722.

General techniques for nucleic acid manipulation useful for the practice of the claimed invention are described generally, for example, in Sambrook et al., *Molecular Cloning: A Laboratory Manual*, Vols. 1–3 (Cold Spring Harbor Laboratory Press, 2 ed., (1989); or F. Ausubel et al., *Current Protocols in Molecular Biology* (Green Publishing and Wiley-Interscience: New York, 1987) and periodic updates. Reagents useful in nucleic acid manipulation, such as restriction enzymes, T7 RNA polymerase, DNA ligases and so on are commercially available from such vendors as New England BioLabs, Boerhinger Mannheim, Amersham, Promega Biotec, U.S. Biochemicals, and New England Nuclear.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride calcium phosphate; DEAE-dextran, or other substances; microprojectile bombardment; lipofection; and infection (where the vector is an infectious agent, such as a retroviral genome). See generally, Sambrook et al., supra and Ausubel et al., supra.

The recombinant host cell may be eukaryotic or prokaryotic, although prokaryotic host cells are preferred for the production of the variant IGFBP-3s of the invention. Among prokaryotic hosts, gram negative bacteria are preferred, especially *Escherichia coli*. Other prokaryotes, such as *Bacillus subtilis* or Pseudomonas may also be used. Mammalian or other eukaryotic host cells, such as yeast, filamentous fungi, plant, insect, amphibian or avian species may also be used. See, *Tissue Culture* (Kruse and Patterson, ed., Academic Press, 1973). Useful mammalian host cell lines include, but are not limited to, VERO and HeLa cells, Chinese hamster ovary (CHO) cells, and W138, BHK, and COS cell lines.

Once a recombinant host cell strain has been established (i.e., the expression construct has been introduced into the host cell and host cells with the proper expression construct are isolated), the recombinant host cell strain is cultured under conditions appropriate for production of the variant IGFBP-3. As will be apparent to one of skill in the art, the method of culture of the recombinant host cell strain will be dependent on the nature of the expression construct utilized and the identity of the host cell. Recombinant host strains are normally cultured in liquid medium containing assimilatable sources of carbon, nitrogen, and inorganic salts, using methods that are well known to the art. Transformed insect or mammalian cells are cultured in liquid medium containing assimilatable sources of carbon, nitrogen, and inorganic salts and, optionally, containing vitamins, amino acids, growth factors, and other proteinaceous culture supplements known to the art. Liquid media for culture of host cells may optionally contain antibiotics or antifungals to prevent the growth of undesirable microorganisms and/or compounds including, but not limited to, antibiotics to select for host cells containing the expression vector.

Recombinant host cells may be cultured in batch or continuous formats, with either cell harvesting (in the case where the variant IGFBP-3 accumulates intracellularly) or harvesting of culture supernatant in either batch or continuous formats. For production in prokaryotic host cells, batch culture and cell harvest are preferred.

The variant IGFBP-3s of the invention are normally purified after expression in recombinant systems. Variant IGFBP-3 may be purified from host cells by a variety of methods known to the art. Normally, variant IGFBP-3 produced in bacterial host cells is poorly soluble or insoluble (in the form of inclusion bodies). In the case of insoluble protein, the protein may be collected from host cell lysates by centrifugation. In the case of poorly soluble protein, compounds including, but not limited to, polyethylene imine (PEI) may be added to induce the precipitation of partially soluble protein. The precipitated protein may then be conveniently collected by centrifugation.

Insoluble or precipitated variant IGFBP-3 may then be solubilized using any of a number of agents known to the art. Preferably, IGF-I or IGFBP-3 is solubilized with urea or guanidine hydrochloride.

When variant IGFBP-3 is produced as a fusion protein, the fusion sequence is preferably removed. Removal of a fusion sequence may be accomplished by enzymatic or chemical cleavage, preferably by enzymatic cleavage. Enzymatic removal of fusion sequences may be accomplished using methods well known to those in the art. The choice of enzyme for removal of the fusion sequence will be determined by the identity of the fusion, and the reaction conditions will be specified by the choice of enzyme as will be apparent to one skilled in the art. The cleaved variant IGFBP-3 is preferably purified from the cleaved fusion sequence by well known methods. Such methods will be determined by the identity and properties of the fusion sequence and the variant IGFBP-3, as will be apparent to one skilled in the art. Methods for purification may include, but are not limited to, size-exclusion chromatography, hydrophobic interaction chromatography, ion-exchange chromatography, or dialysis.

Variant IGFBP-3 is also preferably purified to remove DNA from the protein solution. DNA may be removed by any of several methods known to the art, such as precipitation or ion exchange chromatography, but is preferably removed by precipitation with protamine sulfate. Variant IGFBP-3 may be separated from the precipitated DNA using methods including centrifugation or filtration.

In the case of prokaryotic production of variant IGFBP-3, the variant IGFBP-3 thus produced is frequently completely or mostly misfolded and thus lacks any biological activity. The bioactivity of the protein may be restored by "refolding". In general, rinsfolded variant IGFBP-3 is refolded by solubilizing (where the variant IGFBP-3 is also insoluble), unfolding and reducing the polypeptide chain using one or more chaotropic agents (e.g., urea and/or guanidine) and an agent capable of reducing disulfide bonds (e.g., dithiothreitol, DTT or 2-mercaptoethanol, 2-ME). At a moderate concentration of chaotrope, an oxidizing agent is added (e.g., oxygen, cystine or cystamine), which allows the reformation of intrachain disulfide bonds. Variant IGFBP-3 may be refolded using standard methods known in the art, such as those described in U.S. Pat. Nos. 4,511,502, 4,511, 503, and 4,512,922. Alternately, be refolded in a cofolding reaction with IGF, such as described in International Patent Application No. WO 96/40736 (Ser. No. PCT/US96/08113).

After refolding, the variant IGFBP-3 is preferably further purified. Purification of variant IGFBP-3 may be accomplished using a variety of techniques well known to the art, including hydrophobic interaction chromatography, size exclusion chromatography, ion exchange chromatography, reverse-phase high performance liquid chromatography, affinity chromatography, and the like. Preferably, native variant IGFBP-3 complex is purified by cation exchange chromatography using a sulfopropyl-derivatized column chromatography matrix,(e.g., SP-Sephadex, Pharmacia, Uppsala, Sweden). Additional purification may also include a step of drying or precipitation of the purified protein.

After purification, variant IGFBP-3 may be exchanged into different buffers and/or concentrated by any of a variety of methods known to the art, including, but not limited to, diafiltration and dialysis.

The purified variant IGFBP-3 is preferably at least 90% pure (as measured by reverse phase high performance liquid chromatography, RP-HPLC, or sodium dodecyl sulfate-polyacrylamide gel electrophoresis, SDS-PAGE) or at least 95% pure, more preferably at least 98% pure, most preferably at least 99% pure. Regardless of the exact numerical value of the purity of the variant IGFBP-3, the variant IGFBP-3 is preferably sufficiently pure for use as a pharmaceutical product.

IGFs, including native IGF-I and IGF-II as well as variant IGFs such as null IGFs, may be produced by any method known in the art, and are preferably produced by recombinant methods, preferably utilizing prokaryotic host cells as described in International Patent Application No. WO 96/40722. Where the IGFs are produced in insoluble and/or misfolded form, the IGFs may be refolded using any of the methods described for the refolding of proteins in general, or they may be refolded using methods specifically disclosed for IGF, such as that disclosed in U.S. Pat. Nos. 5,288,931, 5,410,026, 5,663,304, or the IGF may be refolded with IGFBP, such as disclosed in U.S. Pat. No. 5,683,980 and International Patent Application No. WO 96/40722.

Preferably, the IGF used for complex formation with the variant IGFBP-3s of the invention is at least partially purified. The binary complex of IGF and variant IGFBP-3 may be, and preferably is, further purified after formation of the complex, utilizing any method known in the art. The exact methods and conditions for purification of the IGF/variant IGFBP-3 complex will vary, depending on the form of the IGF and the particular IGFBP-3 variant used, as will be apparent to one of skill in the art.

Certain variant IGFBP-3s (e.g., hydrolysis-resistant IGFBP-3 and NLS variant IGFBP-3) may be used as therapeutic agents in the absence of other proteins (other than excipients, carriers, and stabilizers, e.g., serum albumin), or they may be complexed with an IGF. The IGF may be native sequence IGF-I, IGF-II, or an IGF variant such as a null IGF. The formation of complexes of variant IGFBP-3s and IGF is accomplished by simply mixing the two proteins in solution. Variant IGFBP-3s retain their IGF and ALS binding capacity, so that administration of the binary complex of IGF/IGFBP-3 to a subject will result in the formation IGF/IGFBP-3/ALS ternary complex. The ternary complex has a long half-life in circulation, much greater than the half life of either IGF or IGFBP-3, or the binary complex.

N-terminal extended IGFBP-3s will normally be administered as a complex of IGF and variant IGFBP-3. For certain N-terminal extended IGFBP-3s, the IGF/variant IGFBP-3 complex will be administered as a complex with a third compound. In the case where a nucleotide binding sequence is the N-terminal extension, the binary complex will further include a therapeutic nucleotide. In the case that the nucleotide binding sequence is a sequence-specific nucleotide binding sequence, the therapeutic nucleotide that is included in the complex will contain a sequence (the "binding target sequence") to which the sequence specific nucleotide binding sequence binds. For example, if the nucleotide binding sequence is the MAT α2 homeodomain, the therapeutic nucleotide will preferably comprise the sequence 5'-ACATGTAATT-3' (SEQ ID NO:2) or variants thereof to which the MAT α2 homeodomain will bind. However, the therapeutic nucleotide need not contain a binding target sequence if the nucleotide binding sequence is not sequence specific.

N-terminal extended IGFBP-3s which comprise a peptide binding sequence or a specific binding member are also administered complexed to IGF and a third compound. In this case, the third compound is a peptide, protein, or other compound which binds to the N-terminal extension. The binding between the N-terminal extension may be specific (as in a specific binding member) or non-specific, as is the case where a peptide binding sequence is the N-terminal extension.

EXAMPLES

Example 1

Expression Constructs for NLS Variant IGFBP-3

A DNA construct encoding a NLS variant IGFBP-3 (K228E,R230G Ala$_5$ ND variant IGFBP-3) was created by polymerase chain reaction site-directed mutagenesis. pKN72249 (which includes a DNA sequence encoding ND variant Ala$_5$ IGFBP-3) was used as the template for two different PCR reactions, one using primers NLSF (5'-CAATGCCGTCCGAGTGAGGGTGGTAAACGAGGT-TTTTGTTGGTG-3') (SEQ ID NO:3) and CYC5'R (5'-CTCCAGTTCGATGTTACCAGCTGAGG-3') (SEQ ID NO:4), and a second using NLSR (5'-ACAAAAACCTCGTTTACCACCCTCACTCGGACGG-CATTGTTTC-3') (SEQ ID NO:5) and BP3 #1 (5'-TTCATCCGTTGCACTCT-3') (SEQ ID NO:6). Amplification was performed according to the manufacturers instructions. 1 μl aliquots from each reaction were re-amplified using primers BP3 #1 and CYC5'R to produce a 0.8 kb amplification product (which was expected to contain a mixture of NLS variant IGFBP-3 DNA).

The 0.8 kb amplification product was purified by agarose gel electrophoresis and Geneclean® (Bio101, La Jolla, Calif.), then digested with SalI and NsiI restriction enzymes. The restriction digest products were run out on an agarose gel and the 0.25 kb product was isolated (this fragment contains the sequence encoding the NLS region of IGFBP-3) by gel electrophoresis. pDM46908 was also digested with SalI and NsiI and the 4.6 kb vector backbone (also containing the remainder of the IGFBP-3 sequence) was isolated by gel electrophoresis.

The two isolated DNA fragments were ligated, then transformed into E. coli strain JM109 and cultured on nutrient media containing ampicillin (pDM46908 carries the bla gene). Several ampicillin resistant clones were selected, and plasmid DNA minipreps were prepared. Miniprep DNA was digested with BamHI and NsiI, which would produce a diagnostic 1.4 kb band from properly ligated plasmids. A single isolate (designated 1–2) with the correct BamHI/NsiI restriction digest was selected for further characterization.

The NLS region of the DNA was sequenced using BP3 #1 as the sequencing primer, to check that the 1–2 isolate had the expected sequence. After the correct sequence was confirmed, the 1–2 isolate was used as source DNA for creation of an expression construct for production of NLS variant Ala$_5$ ND variant IGFBP-3.

A 0.25 kb SalI-NsiI fragment from the NLS isolate 1–2 was ligated in a three-way reaction with a 1.2 kb XbaI/SalI fragment from pKN72253 and a 5.5 kb XbaI/NsiI fragment from pDJ12887, creating a plasmid essentially identical to pDM46884-BP3 (Zhang et al. 1998, Prot. Exp. Purif. 12:159–165) except that the IGFBP-3 sequence was replaced with the new NLS variant Ala$_5$ ND variant IGFBP-3 sequence. The ligation reaction was transformed into JM109 and the transformed cells were cultured on nutrient media containing ampicillin and tetracycline. Several clones were isolated and screened by XbaI/NsiI digestion of miniprep DNA (a correct ligation was expected to result in a diagnostic 1.4 kb fragment). One clone yielding the proper restriction digest pattern was selected and plasmid DNA was prepared. The plasmid DNA was transformed into E. coli SB1076 for expression of the NLS variant IGFBP-3.

The patents, patent applications and publications cited throughout the disclosure are incorporated herein by reference in their entirety.

The present invention has been detailed both by direct description and by example. Equivalents and modifications of the present invention will be apparent to those skilled in the art, and are encompassed within the scope of the invention.

What is claimed is:

1. An isolated hydrolysis-resistant IGFBP-3, comprising SEQ ID NO: 1 or a variant thereof, wherein position 116 is changed to glutamic acid.

2. An isolated hydrolysis-resistant IGFBP-3, comprising SEQ ID NO: 1 or a variant thereof, wherein position 135 is changed to an amino acid other than aspartate.

3. The hydrolysis-resistant IGFBP-3 of claim 2, wherein position 135 is changed to glutamic acid.

4. The hydrolysis-resistant IGFBP-3 of claim 3, wherein residue 116 is changed to an amino acid other than aspartate.

5. The hydrolysis-resistant IGFBP-3 of claim 4, wherein residue 116 is changed to glutamic acid.

6. An isolated nuclear localization signal (NLS) variant IGFBP-3 (SEQ ID NO: 1) selected from the group consisting of variants wherein:
   residue 215 is altered to an amino acid other than lysine;
   residue 216 is altered to an amino acid other than lysine; and
   residue 228 is altered to glutamic acid.

7. The NLS variant IGFBP-3 of claim 6, wherein residue 230 is altered to an amino acid other than arginine.

8. The NLS variant IGFBP-3 of claim 7, wherein residue 230 is altered to glycine.

* * * * *

SEQUENCE LISTING

<160> NUMBER OF SEQ ID NOS: 6

<210> SEQ ID NO 1
<211> LENGTH: 264
<212> TYPE: PRT
<213> ORGANISM: Homo sapien

<400> SEQUENCE: 1

Gly Ala Ser Ser Ala Gly Leu Gly Pro Val Val Arg Cys Glu Pro Cys
 1               5                  10                  15

Asp Ala Arg Ala Leu Ala Gln Cys Ala Pro Pro Ala Val Cys Ala
                20                  25                  30

Glu Leu Val Arg Glu Pro Gly Cys Gly Cys Cys Leu Thr Cys Ala Leu
                35                  40                  45

Ser Glu Gly Gln Pro Cys Gly Ile Tyr Thr Glu Arg Cys Gly Ser Gly
            50                  55                  60

Leu Arg Cys Gln Pro Ser Pro Asp Glu Ala Arg Pro Leu Gln Ala Leu
 65                  70                  75                  80

Leu Asp Gly Arg Gly Leu Cys Val Asn Ala Ser Ala Val Ser Arg Leu
                85                  90                  95

Arg Ala Tyr Leu Leu Pro Ala Pro Pro Ala Pro Gly Asn Ala Ser Glu
                100                 105                 110

Ser Glu Glu Asp Arg Ser Ala Gly Ser Val Glu Ser Pro Ser Val Ser
                115                 120                 125

Ser Thr His Arg Val Ser Asp Pro Lys Phe His Pro Leu His Ser Lys
            130                 135                 140

Ile Ile Ile Lys Lys Gly His Ala Lys Asp Ser Gln Arg Tyr Lys
145                 150                 155                 160

Val Asp Tyr Glu Ser Gln Ser Thr Asp Thr Gln Asn Phe Ser Ser Glu
                165                 170                 175

Ser Lys Arg Glu Thr Glu Tyr Gly Pro Cys Arg Arg Glu Met Glu Asp
                180                 185                 190

Thr Leu Asn His Leu Lys Phe Leu Asn Val Leu Ser Pro Arg Gly Val
                195                 200                 205

His Ile Pro Asn Cys Asp Lys Lys Gly Phe Tyr Lys Lys Lys Gln Cys
                210                 215                 220

Arg Pro Ser Lys Gly Arg Lys Arg Gly Phe Cys Trp Cys Val Asp Lys
225                 230                 235                 240

Tyr Gly Gln Pro Leu Pro Gly Tyr Thr Thr Lys Gly Lys Glu Asp Val
                245                 250                 255

His Cys Tyr Ser Met Gln Ser Lys
                260

<210> SEQ ID NO 2
<211> LENGTH: 10
<212> TYPE: DNA
<213> ORGANISM: Saccharomyces cerevisiae

<400> SEQUENCE: 2
acatgtaatt                                                          10

<210> SEQ ID NO 3
<211> LENGTH: 44
<212> TYPE: DNA

```
<213> ORGANISM: Artificial Sequence
<220> FEATURE:
<223> OTHER INFORMATION: synthetic construct

<400> SEQUENCE: 3
caatgccgtc cgagtgaggg tggtaaacga ggttttttgtt ggtg         44

<210> SEQ ID NO 4
<211> LENGTH: 26
<212> TYPE: DNA
<213> ORGANISM: Artificial Sequence
<220> FEATURE:
<223> OTHER INFORMATION: synthetic construct

<400> SEQUENCE: 4
ctccagttcg atgttaccag ctgagg                              26

<210> SEQ ID NO 5
<211> LENGTH: 43
<212> TYPE: DNA
<213> ORGANISM: Artificial Sequence
<220> FEATURE:
<223> OTHER INFORMATION: synthetic construct

<400> SEQUENCE: 5
acaaaaacct cgtttaccac cctcactcgg acggcattgt ttc           43

<210> SEQ ID NO 6
<211> LENGTH: 17
<212> TYPE: DNA
<213> ORGANISM: Artificial Sequence
<220> FEATURE:
<223> OTHER INFORMATION: synthetic construct

<400> SEQUENCE: 6
ttcatccgtt gcactct                                        17
```